United States Patent [19]

Bolanos et al.

[11] Patent Number: 5,462,555
[45] Date of Patent: Oct. 31, 1995

[54] UMBILICAL CORD CLIP AND APPLICATOR

[75] Inventors: Henry Bolanos, East Norwalk; Ghaleb A. Sater, Shelton; Stephan A. DeFonzo, Bridgeport, all of Conn.; Wayne P. Young, Brewster, N.Y.

[73] Assignee: United States Surgical Corporation, Norwalk, Conn.

[21] Appl. No.: 175,816

[22] Filed: Dec. 30, 1993

[51] Int. Cl.⁶ .................................................. A61B 17/12
[52] U.S. Cl. ........................................ 606/120; 606/151
[58] Field of Search ............................... 606/1, 110–112, 606/118–120, 135–137, 142, 151, 157, 167, 172

[56] References Cited

U.S. PATENT DOCUMENTS

| | | |
|---|---|---|
| D. 190,787 | 6/1961 | Schneider . |
| D. 323,890 | 2/1992 | Collins . |
| 352,245 | 11/1886 | Hullborst . |
| 600,887 | 3/1898 | Pettit . |
| 640,517 | 1/1990 | Acheson . |
| 643,003 | 2/1900 | Pollock . |
| 789,401 | 5/1905 | Acheson . |
| 1,440,574 | 1/1923 | Ziegler . |
| 1,560,687 | 10/1925 | Hauber . |
| 1,630,031 | 5/1927 | Rogers . |
| 1,683,119 | 9/1928 | Ziegler . |
| 1,708,432 | 4/1929 | Sprigg . |
| 1,710,766 | 4/1929 | Dilworth . |
| 1,843,652 | 2/1932 | Taylor . |
| 1,983,969 | 12/1934 | Davis . |
| 2,013,269 | 9/1935 | Ginsburg . |
| 2,052,870 | 9/1936 | Coco . |

(List continued on next page.)

FOREIGN PATENT DOCUMENTS

| | | |
|---|---|---|
| 1534916 | 6/1968 | France . |
| 2525650 | 12/1976 | Germany . |
| 1335672 | 10/1973 | United Kingdom . |
| WO85/04091 | 9/1985 | WIPO . |
| WO86/02541 | 5/1986 | WIPO . |
| WO89/05125 | 6/1989 | WIPO . |
| 9216150 | 10/1992 | WIPO .................................... 606/120 |

OTHER PUBLICATIONS

Fist, Harry S. M.D., A Simple Umbilical Cord Clamp, 1930, American Journal of Ostetrics Gynecology, p. 135.
United Surgical Co., Umbilical Closure, Feb. 1970 MSR, p. 23.
Jacobs, J. Bay, M.D., Disposable Cord Clamp That Establishes unmistakable Identification of the Newborn, Reprinted from American Journal of Obstetrics And Gynecology, vol. 25, No. 7, pp. 425–427, Feb., 1958.

Primary Examiner—Stephen C. Pellegrino
Assistant Examiner—Glenn Dawson

[57] ABSTRACT

An umbilical cord clip and applicator is disclosed for clamping a maternal side of an umbilical cord, applying an umbilical cord clip to a fetal side of the umbilical cord and severing the cord intermediate the clamped maternal and fetal sides of the umbilical cord. The applicator includes a first arm having a first clamping surface, a second arm movably affixed to the first arm and having a second clamping surface and structure associated with at least one the first and second arms for mounting an umbilical cord clip thereon. The applicator also includes a recessed severing mechanism operatively associated with the first and second arms and disposed intermediate the first and second clamping surfaces and the mounting structure. The severing mechanism is automatically actuable upon closure of the first and second arms about an umbilical cord to sever the cord at a location between the first and second clamping surfaces and the clip. The umbilical cord clip includes a first leg having a first clamping surface and a second leg movably affixed to the first leg and having a second clamping surface. A lock device is associated with the first and second legs for maintaining the first and second legs in a closed position about the umbilical cord. Attachment structure is also associated with at least one of the first and second legs. The attachment structure is releasably engagable with the mounting structure on the applicator to hold the umbilical cord clip on the applicator.

23 Claims, 10 Drawing Sheets

U.S. PATENT DOCUMENTS

| | | | |
|---|---|---|---|
| 2,060,724 | 11/1936 | Carroll . | |
| 2,108,325 | 2/1938 | Ziegler . | |
| 2,114,903 | 4/1938 | Hoppenstand . | |
| 2,307,377 | 1/1943 | Riccardi . | |
| 2,384,697 | 9/1945 | Riccardi . | |
| 2,434,831 | 1/1948 | Brandenburg . | |
| 2,498,372 | 2/1950 | Kortlucke, Jr. et al. . | |
| 2,524,337 | 10/1950 | Whittaker . | |
| 2,556,036 | 6/1951 | Jensen | 606/167 |
| 2,598,901 | 6/1952 | Garland . | |
| 2,626,608 | 1/1953 | Garland . | |
| 2,635,238 | 4/1953 | Garland . | |
| 2,686,520 | 8/1954 | Jarvis, et al. . | |
| 2,973,761 | 3/1961 | Kohl . | |
| 3,016,056 | 1/1962 | Jacobs . | |
| 3,040,749 | 6/1962 | Payton . | |
| 3,106,919 | 10/1963 | Churchville . | |
| 3,150,666 | 9/1964 | Averbach . | |
| 3,166,071 | 1/1965 | Mayer . | |
| 3,171,184 | 3/1965 | Posse . | |
| 3,204,636 | 9/1965 | Kariher et al. . | |
| 3,247,852 | 4/1966 | Schneider . | |
| 3,315,679 | 4/1967 | Sarracino . | |
| 3,323,208 | 6/1967 | Hurley, Jr. . | |
| 3,566,873 | 3/1971 | Melges | 606/111 |
| 3,576,054 | 4/1971 | Rynk . | |
| 3,631,858 | 1/1972 | Ersek . | |
| 3,674,032 | 7/1972 | Minganti . | |
| 3,705,586 | 12/1972 | Sarracino . | |
| 3,706,312 | 12/1972 | Melges | 606/157 |
| 3,766,925 | 10/1973 | Rubricius . | |
| 3,825,012 | 7/1974 | Nicoll . | |
| 3,854,482 | 12/1974 | Laugherty . | |
| 4,026,294 | 5/1977 | Mattler . | |
| 4,212,303 | 7/1980 | Nolan . | |
| 4,345,600 | 8/1982 | Rothfuss | 606/167 |
| 4,428,374 | 1/1984 | Auburn . | |
| 4,648,401 | 3/1987 | Mattson . | |
| 4,716,886 | 1/1988 | Schulman et al. . | |
| 4,773,431 | 9/1988 | Lodomirski . | |
| 4,781,188 | 11/1988 | Collins . | |
| 4,856,517 | 8/1989 | Collins et al. . | |
| 4,870,965 | 10/1989 | Jahanger . | |
| 4,899,134 | 2/1990 | Wheeless, Jr. . | |
| 4,938,215 | 7/1990 | Schulman et al. . | |
| 5,006,830 | 4/1991 | Merritt . | |
| 5,009,657 | 4/1991 | Cotey et al. . | |
| 5,127,915 | 7/1992 | Mattson . | |
| 5,163,943 | 11/1992 | Mohiudden | 606/118 |
| 5,178,624 | 1/1993 | Kyun . | |
| 5,190,556 | 3/1993 | Hessel . | |

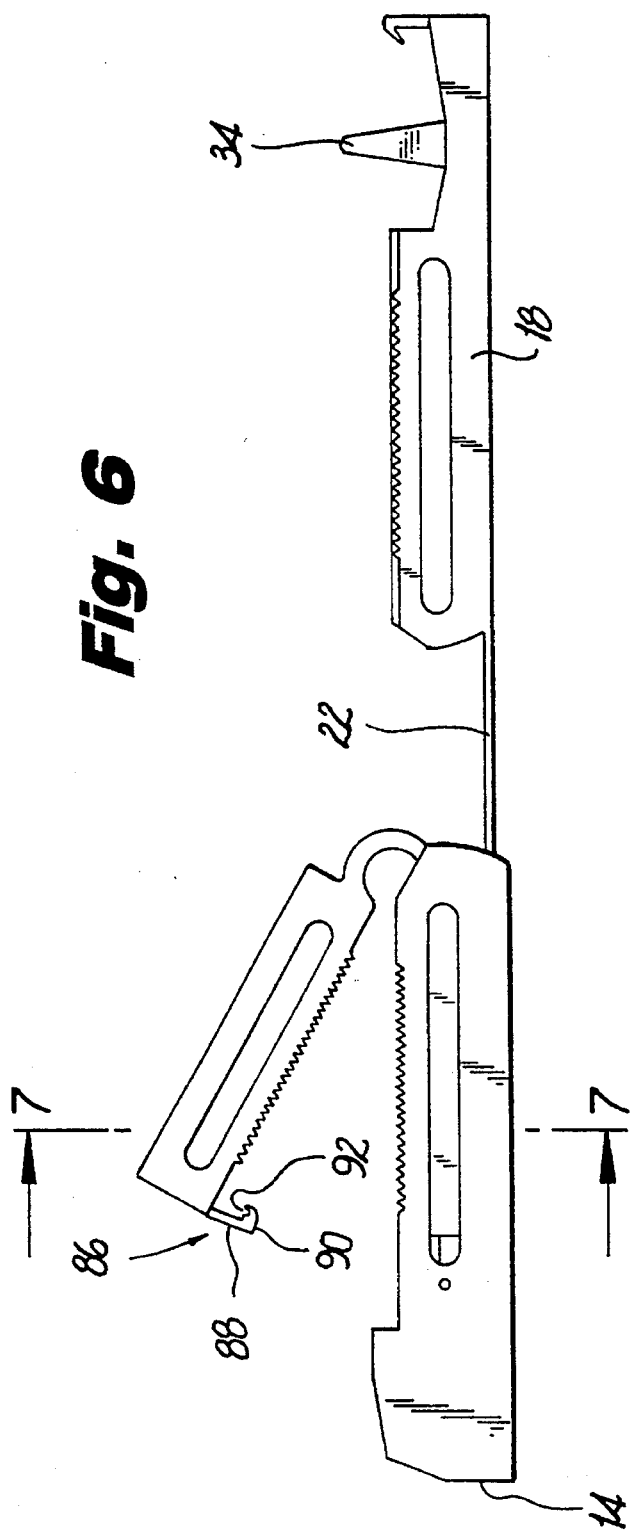
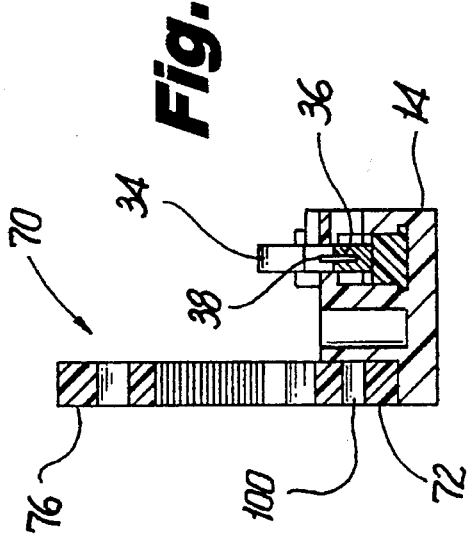

UMBILICAL CORD CLIP AND APPLICATOR

BACKGROUND OF THE INVENTION

1. Field of the Invention

The present invention relates to devices for clamping and severing an umbilical cord and, more particularly, to an umbilical cord clip and an applicator having a concealed blade for safely and automatically severing an umbilical cord.

2. Description of the Related Art

Various surgical instruments have been developed to separate and clamp the umbilical cord joining a newborn infant and its mother. These devices typically cut or sever the umbilical cord between the fetal side of the cord and the maternal side of the cord. More modern instruments are also capable of placing one or more clips or umbilical cord clamps on the fetal and/or maternal sides of the cord.

One instrument for severing an umbilical cord and applying a clamp thereto is disclosed in U.S. Pat. No. 3,323,208 to Hurley, Jr. ("Hurley"). Hurley discloses a two part device including an applicator containing a fixed blade for severing an umbilical cord and a clamp affixed to the applicator for clamping the umbilical cord. The clamp is attached to the applicator by means of pins. Upon severing the cord and the pins, the applicator and knife blade remain clamped to the maternal side of the cord while the clamp is clamped to the fetal side of the cord.

Another device is disclosed in U.S. Pat. No. 3,631,858 to Ersek ("Ersek") which operates similar to the device of Hurley described above. Ersek also employs an exposed fixed knife blade which is used to sever the umbilical cord and separate the maternal and fetal side clamps. The clamps are connected by a web which is severed by the knife blade upon closure of the instrument about the umbilical cord.

A further device used to sever an umbilical cord is disclosed in U.S. Pat. No. 4,648,401 to Mattson ("Mattson"). Mattson discloses a scissor-like device having handle portions and first and second closing jaw portions attached thereto. The Mattson device further includes a replaceable knife blade and a releasable umbilical cord clamp. Hemostatic surfaces are provided on the jaws of the scissor-like instrument to temporarily clamp one side of the umbilical cord while the clamp is applied to an opposing side of the cord and the cord is severed between the clamped portions of the cord.

A device used to apply a pair of clamps to an umbilical cord and sever the cord between the clamps is disclosed in the U.S. Pat. No. 4,856,517 to Collins et al. ("Collins et al."). Collins et al. discloses an applicator having upper and lower portions for applying a pair of umbilical cord clamps, held within recesses in the upper and lower portions, to an umbilical cord. A slidable knife blade is located between the clamps and adapted to be slid, by the thumb of the user, between ends of the upper and lower portions to sever the umbilical cord.

One form of an umbilical cord clamp is illustrated in U.S. Pat. No. 4,212,303 to Nolan ("Nolan"). Nolan shows an umbilical cord clamp having a generally V-shaped configuration including a pair of flexible arms joined together by an integral hinge. Nolan further includes locking means for securing the arms together including a flexible tongue at the forward end of one of the arms engagable with a recess at the forward end of the other arm. A pair of transversely spaced projections extend into the recess and define a pair of forwardly sloping ramp surface engagable with lateral notches in a tip portion of the tongue to hold the arms together.

Another form of an umbilical cord clamp is illustrated in U.S. Pat. No. 3,247,852 to Schneider ("Schneider"). Schneider shows an umbilical cord clamp having a pair of arms joined together by an integral hinge forming loop. A blocking member is positioned within the loop to prevent entry of the cord into the loop upon clamping of the arms. The clamp further includes longitudinally extending grooves within each of the arms to aid in clamping the cord along with means for locking the arms together in a clamped position.

In the above described umbilical cord clamp applicator instruments, the knife blade is exposed to the operator/surgeon prior to clamping the device about an umbilical cord. Thus, in view of the prevalence of various infectious diseases such as AIDS, etc., it is highly desirable to provide an umbilical cord clamp and applicator which conceals the knife blade prior to clamping the device about an umbilical cord and which locks in a closed position to protect the surgeon from cuts and possible resultant infection.

SUMMARY OF THE INVENTION

An apparatus in the form of a surgical instrument is disclosed for clamping a maternal side of an umbilical cord, applying an umbilical cord clip to a fetal side of the umbilical cord and severing the cord between the clamped and clipped sides of the cord. The apparatus is in the form of an applicator including a first arm having a first cord engaging clamping surface and a second arm movably affixed to the first arm and having a second cord engaging clamping surface. Means associated with at least one the first and second arms are provided for mounting at least one umbilical cord clip thereon. There is also provided a recessed severing mechanism operatively associated with the first and second arms and disposed intermediate the first and second clamping surfaces and the mounting means. The severing mechanism is automatically actuable upon closure of the first and second arms about an umbilical cord to sever the cord between the first and second clamping surfaces and the clip. Also disclosed is an umbilical cord clip including a first leg having a first clamping surface and second leg movably affixed to the first leg and having a second clamping surface. Lock means are associated with the first and second legs for maintaining the first and second legs in a closed position about an umbilical cord. Attachment means are associated with at least one of the first and second legs and are releasably engagable with the mounting means to hold the umbilical cord clip on the applicator.

The recessed severing mechanism includes a deflectable knife member movably mounted on the first arm and a projection mounted on second arm and extending towards the first arm. Closure of the first and second arms about the umbilical cord causes the projection to deflect the knife member away from its recessed position in the first arm and towards the second arm to sever the umbilical cord captured between the first and second arms.

The mounting means may include an elongated tab member projecting transversely from at least one of the arms for releasable engagement with mounting means on at least one of the first and second clamping legs of the clip. Alternatively, the mounting means may include a pair of longitudinally spaced pins projecting transversely from the arms and engagable with the corresponding mounting means on the legs. A proximally extending projection formed at a distal end of at least one of the first and second arms and engagable with at least a portion of the lock means on the clip may also be provided to maintain the clip in position on said surgical instrument.

Preferably, the first and second clamping surfaces of the first and second legs may be ridged to enhance grasping the umbilical cord. Additionally, the first and second legs may be hollowed out beneath the clamping surfaces to provide a degree of flexibility to the clamping surfaces in order to prevent crushing of the umbilical cord upon clamping.

BRIEF DESCRIPTION OF THE DRAWINGS

Preferred embodiments of the invention are described herein below with reference to the drawings wherein;

FIG. 6 is a side view of the applicator of FIG. 2;

FIG. 7 is an end view of the applicator of FIG. 2 taken along the lines 7—7 of FIG. 6;

DETAILED DESCRIPTION OF THE PREFERRED EMBODIMENTS

Figure 1:
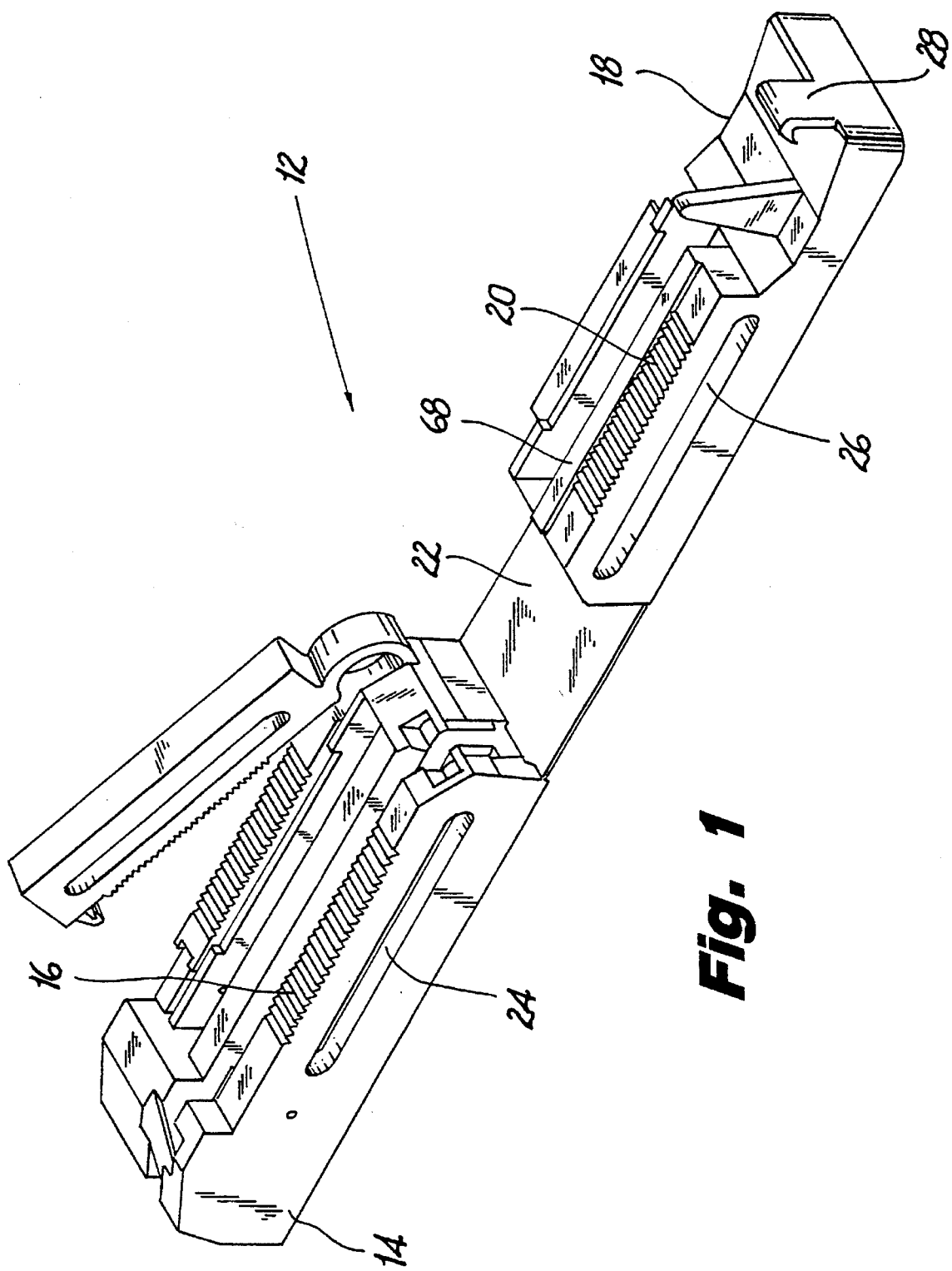
FIG. 1 is a reverse perspective view of an umbilical cord clip applicator in accordance with one embodiment of the present invention.

One embodiment of the applicator and umbilical cord clip of the present invention is illustrated in FIGS. 1–10. Referring to FIG. 1, applicator 12 generally includes a first clamping arm 14 having a first clamping surface 16 and a second clamping arm 18 having a second clamping surface 20. First and second clamping arms 14 and 18, respectively, are flexibly joined together by a living hinge 22 which allows arms 14 and 18 of applicator 12 to be bent or folded over an umbilical cord (not shown) to capture and hold the cord between first and second clamping surfaces 16 and 20, respectively. Additionally, other known forms of movably joining arms 14 and 18, such as, for example, hinges and pins, may be provided.

Preferably, first clamping surface 16 and second clamping surface 20 include ridges or a roughened texture to improve the gripping ability about the umbilical cord. In order to prevent crushing of the umbilical cord during clamping, first and second clamping arms 14 and 18 may further be provided with grooved or hollowed out areas 24 and 26 located below clamping surface 16 and 20, respectively. Hollowed areas 24 and 26 extend transversely through arms 14 and 18, respectively, provide a degree of flexibility or resiliency to clamping surfaces 16 and 20 allowing surfaces 16 and 20 to flex around an umbilical cord held therebetween. Preferably, applicator 12 is formed of a polymeric material such as, for example polyethylene. Arms 14 and 18 are each preferably approximately 10 cm long by 2.5 cm wide.

Figure 4:
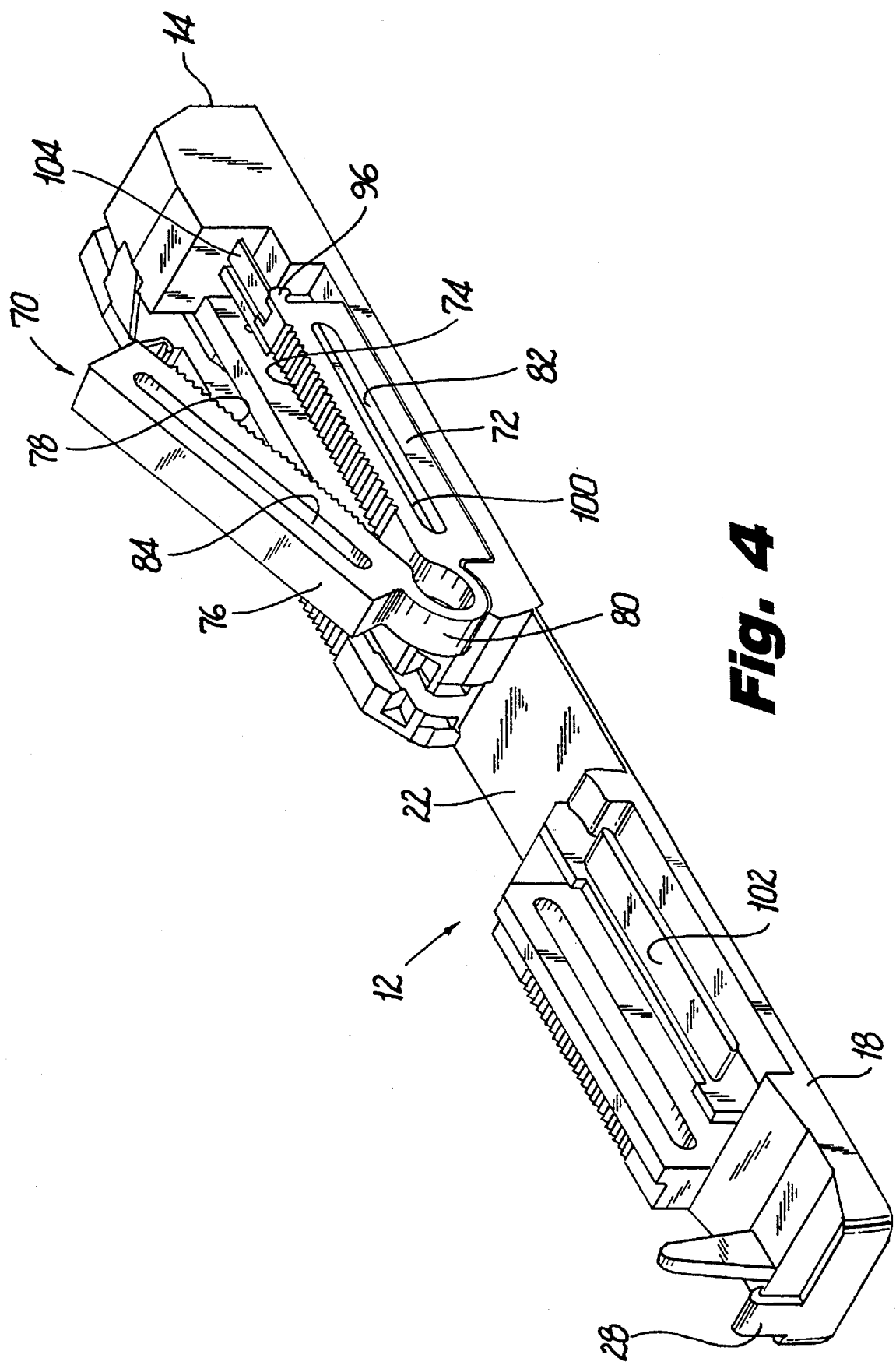
FIG. 4 is a perspective view of the applicator of FIG. 2 illustrating the clip retaining side of the apparatus.
Figure 5:
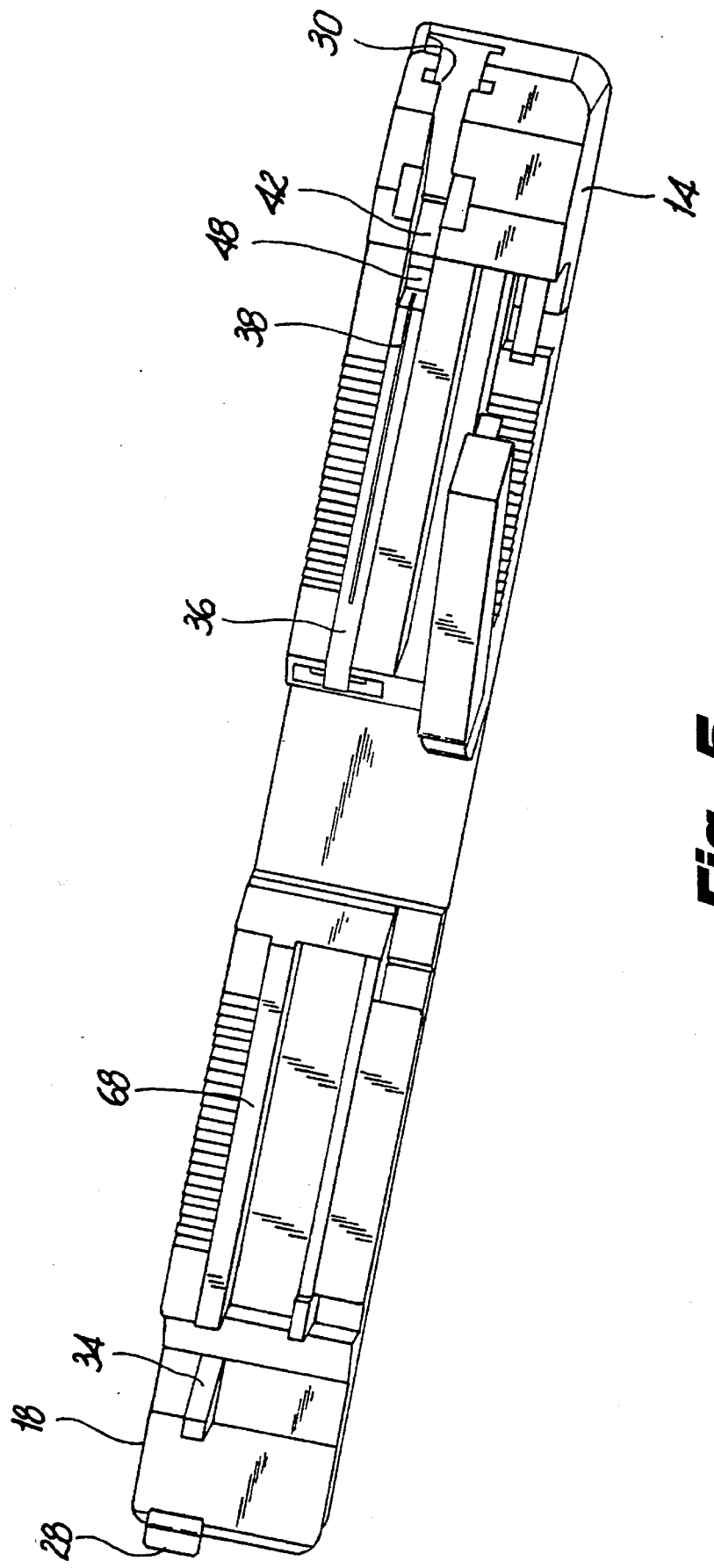
FIG. 5 is a top isometric view of the applicator of FIG. 2.

Referring now to FIGS. 1 and 5, applicator 12 may be provided with a latch mechanism to hold arms 14 and 18 closed about an umbilical cord. The latch mechanism includes a prong 28 formed on an end of second clamping arm 18. Prong 28 is engagable with a recess 30 (FIG. 4) formed in an end of first arm 14 to hold arms 14 and 18 together in a closed position.

Figure 2:
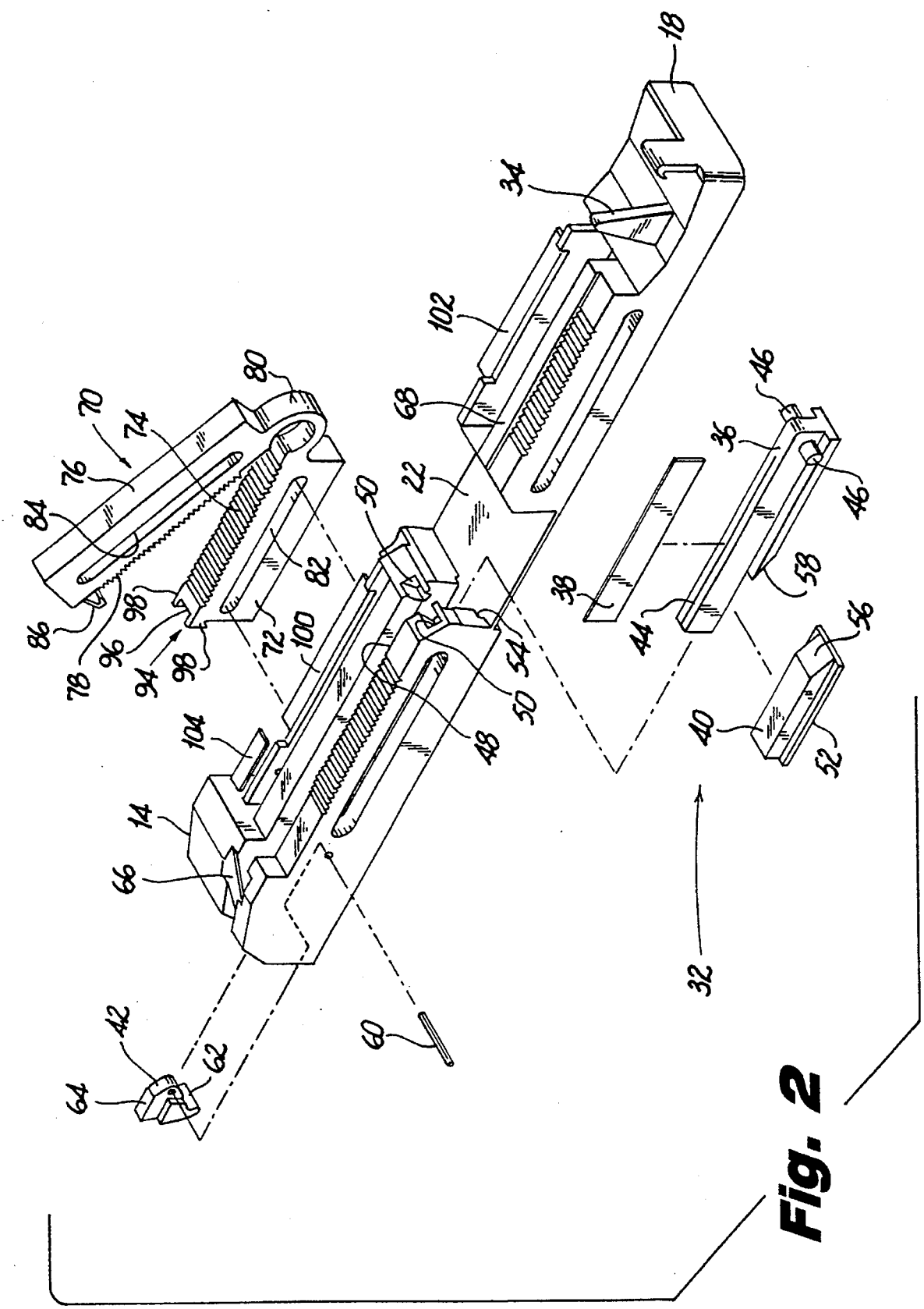
FIG. 2 is an reverse exploded perspective view of the applicator of FIG. 1 having an umbilical cord clip mounted therein.
Figure 8:
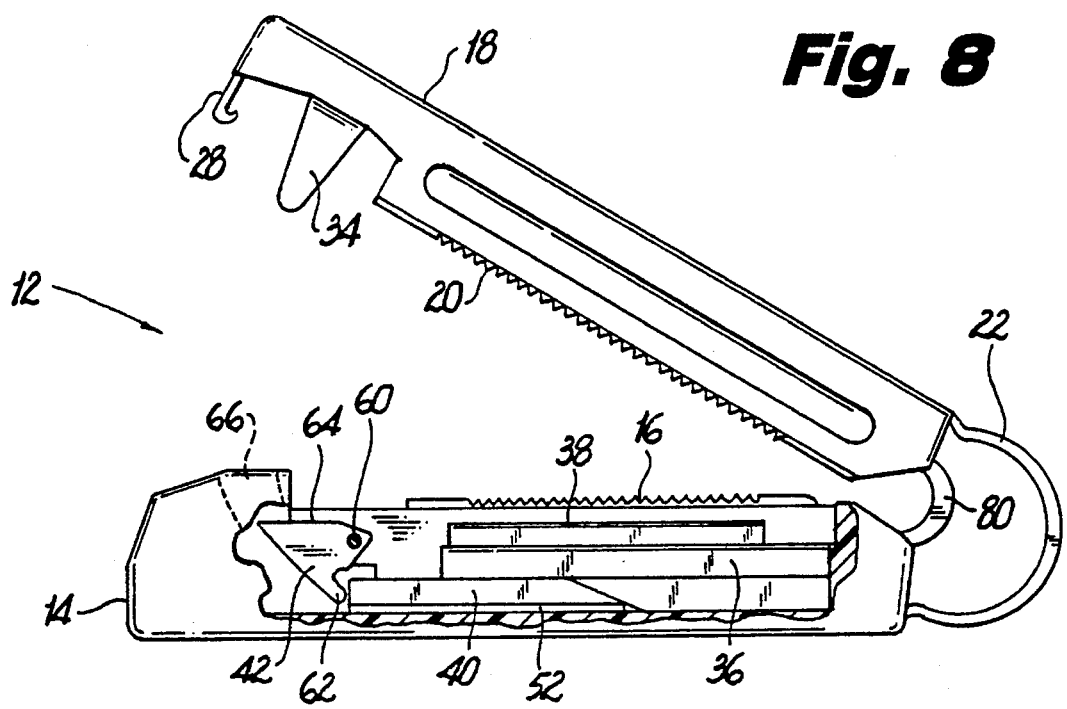
FIG. 8 is a side view, partially shown in section, of the applicator of FIG. 2 in an open position showing the knife blade disposed within one arm.

Referring now to FIGS. 2 and 8, applicator 12 further includes a recessed severing mechanism which is adapted to remain concealed within first arm 14 until applicator 12 is moved into a closing and clamping position. The recessed umbilical cord severing mechanism generally consists of a movable knife assembly 32 mounted with respect to first arm 14 and an actuation member 34 formed on second arm 18. Knife assembly 32 generally includes a knife carrier 36, a knife blade 38, a slidable wedge 40 and a cam member 42. Knife carrier 36 holds knife blade 38 within slot 44 formed on a top surface of knife carrier 36. Knife carrier 36 further includes a pair of transversely projecting pins 46 formed on a distal end of carrier 36. Carrier 36 is positioned within a slot 48 in first arm 14 such that pins 46 are located in wells 50 in first arm 14. By locating carrier 36 within slot 48, carrier 36 is free to pivot with respect to arm 14 by means of pins 46 to raise and lower knife blade 38 between exposed and recessed positions within slot 48. Additionally, wells 50 allow some degree of vertical travel to pins 46 to further allow carrier 36 to move up and down within slot 48. Preferably, knife carrier 36, slidable wedge 40 and cam member 42 are formed of nylon, while knife blade 38 is formed of stainless steel.

Wedge 40 includes a base 52 which allows wedge 40 to slide longitudinally within a lower portion 54 of slot 48. Wedge 40 further includes an angled camming face 56 which engages a corresponding face 58 on carrier 36 to pivot and drive carrier 36 upwardly as wedge 40 slides proximally. As used herein, proximally refers to a direction towards living hinge 22 while distal refers to a direction away from hinge 22 to reflect the orientation of applicator 12 as arms 14 and 18 are pivoted towards one another in the hand of the user with hinge 22 being proximal to the user.

Cam 42 is provided to drive wedge 40 proximally and is pivotally mounted within slot 48 by means of a pivot pin 60. As cam 42 is pivoted about pin 60, a driving surface 62 on cam 42 engages wedge 40 to slide wedge 40 within slot 48. Cam 42 is pivoted about pin 60 by closing second arm 18 towards first arm 14 causing projection 34 to enter a gap 66 and impinge upon an upper surface 64 of cam 42.

Figure 9:
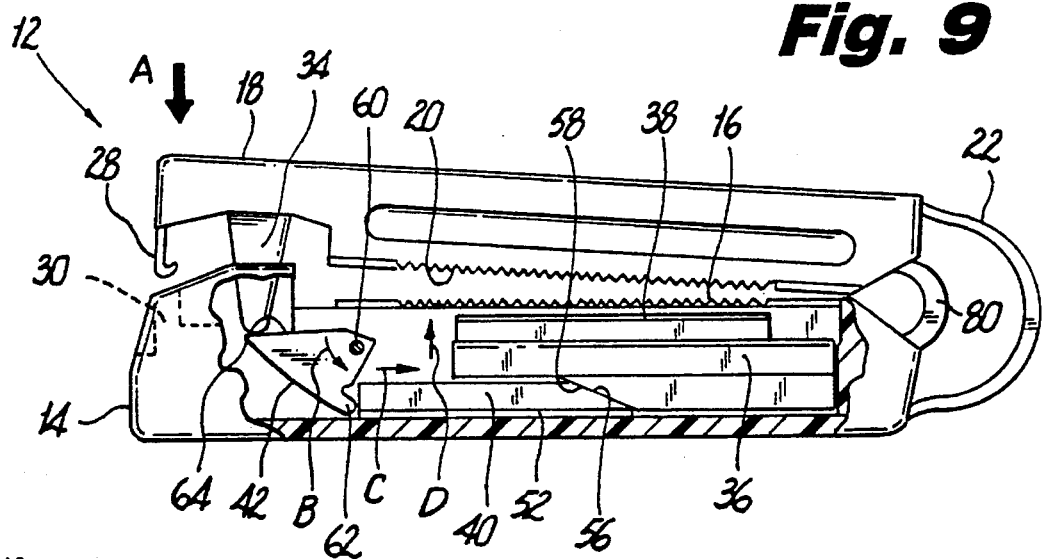
FIG. 9 is a side view, partially shown in section, of the applicator of FIG. 2 in a partially closed position showing partial actuation of the severing mechanism.
Figure 10:
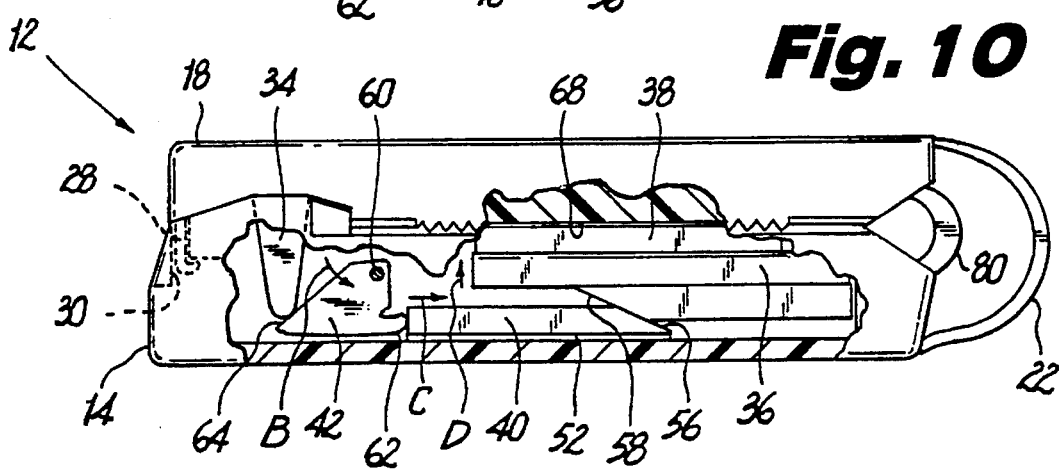
FIG. 10 is a side view, partially shown in section, of the applicator of FIG. 2 in a fully closed position showing the severing mechanism in the fully actuated position.

In this manner it can be seen that knife blade 38 is initially located in a retracted position within slot 48 as shown, for example, in FIGS. 1, 7 and 8. Referring now to FIGS. 9 and 10, second arm 18 is moved towards first arm 14, in the direction of arrow A, to close clamping surfaces 16 and 20 about an umbilical cord (not shown), projection 34 enters gap 66 and pivots cam 42, in the direction of arrow B, to drive wedge 40 proximally beneath knife carrier 36, in the direction of arrow C. Knife carrier 36 pivots or is deflected upwardly raising knife blade 38 up out of slot 48, in the direction of arrow D, to an exposed position out of first arm 14. Knife blade 38 moves upwardly until it contacts a cutting surface 68 formed in second arm 18 (FIGS. 1 and 10). Thus, the safety severing mechanism protects the user from knife blade 38 by concealing blade 38 within first arm 14 until applicator 12 is closed. Further, knife blade 38 is automatically moved or actuated to sever an umbilical cord between blade 38 and cutting surface 68 as clamping surfaces 16 and 20 of applicator instrument 12 are closed about a cord, thereby requiring no additional cutting movements or operations on the part of the user. Thus, the umbilical cord can be safely clamped and automatically severed by one continuous movement on the part of the user.

In using applicator 12 to clamp and sever an umbilical cord at a location between a newborn infant and its mother, applicator 12 is positioned with first and second arms 14 and 18 surrounding the umbilical cord. Still referring to FIGS. 8–10, first and second arms 14 and 18 are closed towards one another to clamp one side, such as, for example, the maternal side, of the umbilical cord (not shown) between clamping surfaces 16 and 20. Arms 14 and 18 are locked together as projection 28 engages recess 30 (FIG. 10) thereby firmly clamping applicator 12 about one side of an umbilical cord. As arms 14 and 18 are being closed together, projection 34 engages cam 42 to drive or deflect knife blade 38 upwardly into cutting surface 60 to sever the umbilical cord positioned therebetween in the manner described herein above. Preferably, the opposing unclamped and now severed side of the umbilical cord, such as, for example, the fetal side, is held by conventional forceps or other grasping devices for later tying or clamping in a known manner. This method may be preferred by surgeons more comfortable with certain cord tying techniques. Thus applicator 12 is particularly suited to safely and automatically sever, and clamp one side of, an umbilical cord without exposing the user to the danger, and possible infection, resulting from a cut from an exposed knife blade.

While applicator 12 may be used alone to clamp and sever an umbilical cord, it is preferable to provide a releasable umbilical cord clip on applicator 12 so that both the maternal and fetal sides of the cord can be clamped and the cord severed therebetween.

Figure 3:
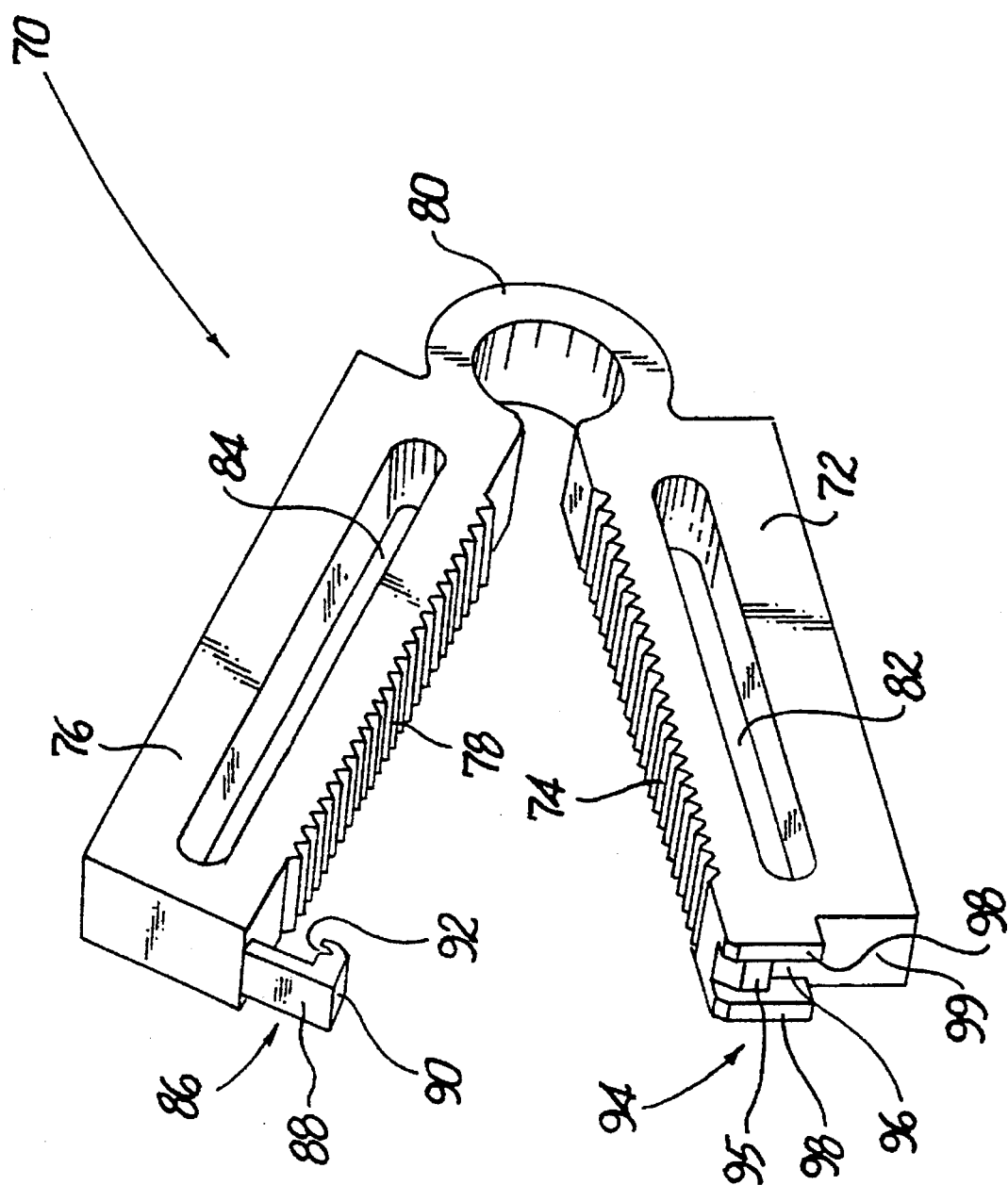
FIG. 3 is a perspective view of an umbilical cord clip for use with the umbilical cord clip applicators of the present invention.

Referring now to FIGS. 2, 3 and 4, one embodiment of an umbilical cord clip 70 includes a first leg 72 having a first inner cord clamping surface 74 and a second leg 76 having a second inner cord clamping surface 78. Legs 72 and 76 are flexibly connected together by a living hinge 80 which biases legs 72 and 76 apart in an unclamped V-shaped configuration. Preferably, clamping surfaces 74 and 78 are also ridged or textured to enhance grasping ability. It may be noted that, while the ridges on clamping surfaces 16, 20,74 and 78 are shown formed transverse to a longitudinal axis of the surfaces, the ridges may also be formed parallel to the respective longitudinal axes, crosswise to the axes, or even in a random arrangement or array. Further, other means of enhancing the grasping action of the clamping surfaces, such as, for example, roughening the surfaces or providing a resilient or adhesive coating are also contemplated within the scope of the invention. Clip 70 is preferably approximately 6 cm long and formed of a polycarbonate material. Legs 72 and 76 may also include grooved or hollowed out portions 82 and 84, respectively, extending transversely through legs 72 and 76. Grooved portions 82 and 84 are located beneath clamping surfaces 74 and 78 to provide a degree of resiliency to the surfaces in order to prevent crushing of the umbilical cord as clip 70 is applied thereto.

As best shown in FIG. 3, umbilical cord clip 70 may also be provided with lock means in the form of a lock tab 86 projecting from a distal end of second leg 76. Lock tab 86 includes a relatively straight portion 88 extending downwardly towards first leg 72, and somewhat proximally, and a hook portion 90 formed on an end of straight portion 88. Hook portion 90 extends proximally and substantially perpendicular to straight portion 88 and terminates in a lip portion 92 extending back upwardly towards second leg 76 in a direction substantially parallel to straight portion 88.

Lock tab 86 is engageable with a lock catch 94 formed on an end of first leg 72. Still referring to FIG. 3, lock catch 94 includes a distally facing projection 95 formed on a distal end of first leg 72. Lock catch 94 includes a pair of transversely spaced and distally facing projections 98 which define a recess 96 therebetween for acceptance of lock tab 86 when clip 70 is in a closed position. Projections 98 further act to align and guide lock tab 86 into engagement with recess 96 of lock catch 94. Projections 98 of lock catch 96 extend sufficiently along a distal face 99 of first leg 72, even when no cord is present and surfaces 74 and 78 are in an abutting relationship, to prevent lock tab 86 from being disengaged from lock catch 94 by moving or twisting second leg 98 transversely relative to first leg 72. This structure helps to prevent accidental release of clip 70 from the clamped maternal or fetal sides of the umbilical cord.

Various means may be provided for mounting and maintaining umbilical cord clip 70 on applicator 12. Referring now to FIGS. 2, 3 and 4, applicator 12 includes mounting means in the form of a pair of transversely projecting mounting tabs 100 and 102 formed on first and second arms 14 and 18, respectively. Tabs 100 and 102 are engagable with grooves 82 and 84, respectively, on umbilical cord clip 70 to maintain clip 70 in position on applicator 12. When mounted on applicator 12, clip 70 causes applicator 12 to assume a partially folded over or V-shaped configuration with clamping surface 16 on first arm 14 facing and slightly spaced apart from clamping surface 20 on second arm 18.

Still referring to FIGS. 2, 3 and 4, additional means in the form of a proximally extending projection 104 formed on first arm 14 may be provided alone, or in conjunction with other mounting means, to maintain umbilical cord clip 70 in position on applicator 12. Projection 104 engages lock catch 94 by extending into recess 96 (FIG. 4). Upon closure of clip 70 about an umbilical cord, lock tab 86 cams projection 104 out of engagement with lock catch 94 to permit disengagement of clip 70 from projection 104.

In a preferred use of applicator 12, an umbilical cord clip, such as clip 70, may be mounted on arms 14 and 18 by means of tabs 100 and 102 as described hereinabove. Clip 70 is held in place by engagement of projection 104 with lock catch 94. Applicator 12, now holding clip 70, is positioned and closed about an umbilical cord as described hereinabove to clamp one side of the cord, such as, for example, the maternal side between clamping surfaces 16 and 20 and automatically sever the cord by moving or deflecting knife blade 38 to sever the cord positioned therebetween and cutting surface 68.

In addition to severing the cord and clamping the maternal side of the cord, closing arms 14 and 18 together also close legs 72 and 76 together to clamp the opposing side, such as, for example, the fetal side, of the cord between clamping surfaces 74 and 78. As noted above, lock tab 86 cams projection 104 out of the way allowing tab 86 to engage lock catch 94, lock clip 70 about the now clamped fetal side of the umbilical cord and release clip 70 from applicator 12. In this manner, both the maternal and fetal sides of an umbilical cord are clamped and the cord is safely and automatically severed therebetween during clamping.

Preferably, applicator 12 and clamp 70 are included for single use only and are provided in a sterile condition. A unit containing applicator 12 and clamp 70 is individually packaged in a thermoformed blister with a TYVEK blister lid. A six unit package may be contained in a multi-pack display box.

Figure 11:
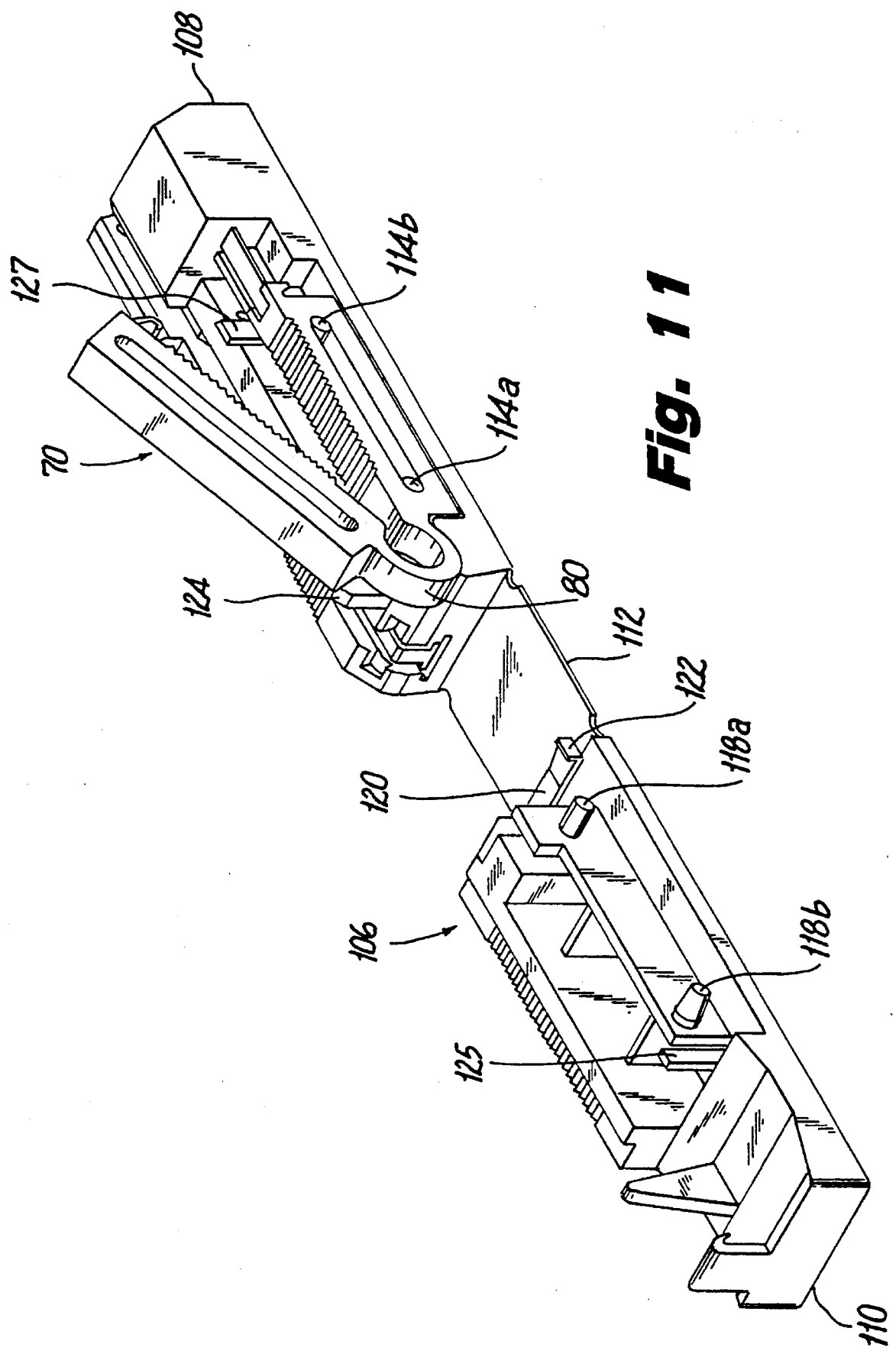
FIG. 11 is a perspective view of an umbilical cord clip applicator in accordance with an alternate embodiment of the present invention.

An alternative embodiment of the present invention is illustrated in FIG. 11. Applicator 106 is similar to applicator 12 and includes a first arm 108 and a second arm 110 connected to first arm 108 by means of a flexible portion or living hinge 112. Applicator 106 is adapted to apply an umbilical cord clip, such as, for example, clip 70 as shown and discussed above. Applicator 106 includes mounting means for holding clip 70, in the form of pairs of longitudinally spaced pins 114(*a* and *b*) and 118(*a* and *b*) projecting transversely from arms 108 and 110 respectively. Pins 114(*a* and *b*) and 118(*a* and *b*) are releasably engagable with ends of grooves 82 and 84, respectively, to maintain clip 70 in place on applicator 106. Preferably, pins 114*a* and 118*a* are substantially cylindrical while pins 114*b* and 118*b* have conical taper to ease the release of clip 70 from applicator 106.

Applicator 106 includes additional means for maintaining clip 70 in place on applicator 106 in the form of a transversely extending projection 102 formed on a proximal end of second arm 110. Projection 120 includes a lip 122 which is engagable with an edge of living hinge 80 on clip 70 when clip 70 is mounted on pins 114*a*, 114*b*, 118*a* and 118*b*. A pusher 124 is formed on a proximal end of first arm 108 to cam projection 120 out of engagement with hinge 80 as arms 108 and 110 are closed about an umbilical cord as described with respect to applicator 12 hereinabove.

Still referring to FIG. 11, means may also be provided to eject clip 70 from applicator 106. For example, a deflectable post 125 may be provided on arm 110 between clip 70 and applicator 106 which cooperates with, and engages, a rigid post 127 formed on opposing arm 108 to cam clip 70 away from applicator 106 as applicator 106 is closed about an umbilical cord.

In use, applicator 106 operates to clamp a maternal side of an umbilical cord, apply clip to a fetal side of the cord and sever the cord therebetween in a manner similar to that described with respect to applicator 12 hereinabove.

Figure 12:
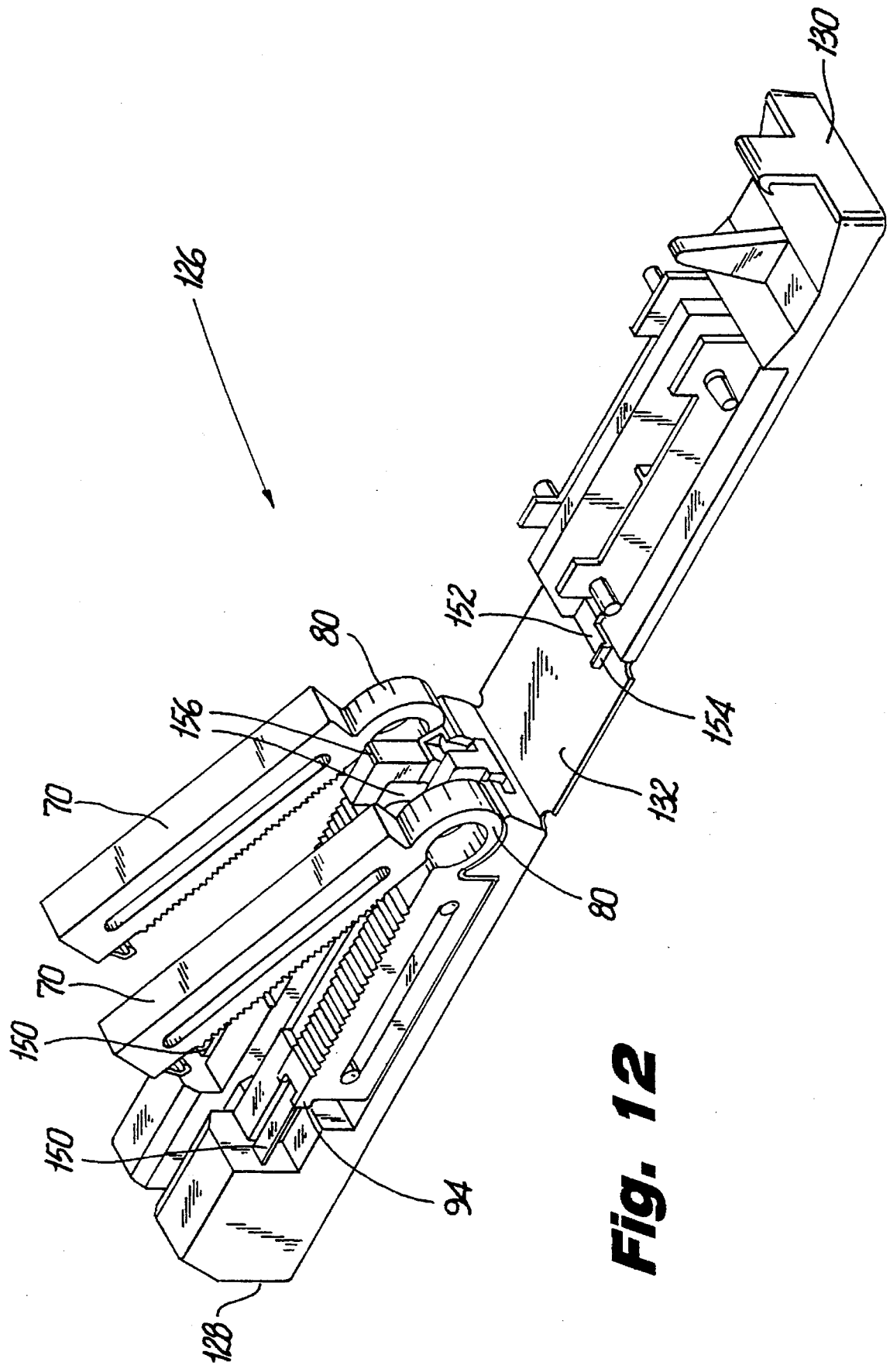
FIG. 12 is a reverse perspective view of an umbilical cord clip applicator in accordance with another embodiment of the present invention.
Figure 13:
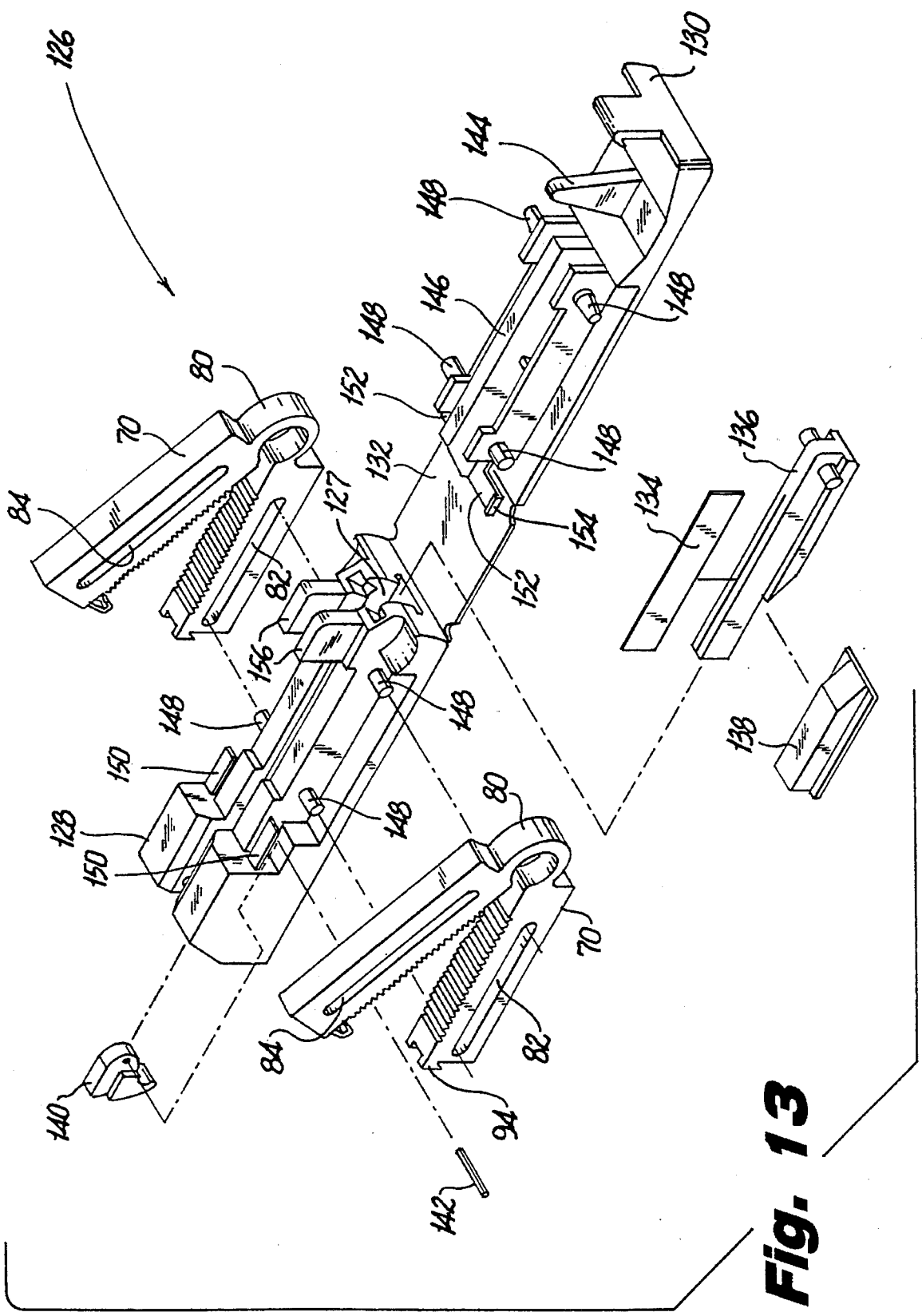
FIG. 13 is an exploded reverse perspective view of the embodiment of FIG. 12.

Referring now to FIGS. 12 and 13, there is shown a further alternative embodiment of the present invention which is adapted to releasably hold two umbilical cord clips, such as, for example clips 70, for clamping the maternal and fetal sides of an umbilical cord and severing the cord between the clips. Applicator 126 is similar to applicator 106 and generally includes a first clip holding arm 128 and a second clip holding arm 130 flexibly affixed to first arm 128 by means of a living hinge portion 132. As shown in FIG. 13, applicator 126 includes a recessed severing mechanism on first arm 128, similar to the severing mechanism of applicator 12 in FIG. 2, having a knife blade 134, a knife carrier 136, a wedge 138 and a cam 140 and cam pin 142. The severing mechanism fits in a slot 127 in arm 128 and cooperates with projection 144 on second arm 130 in a manner identical to knife assembly 32 and projection 34 described with respect to applicator 12 hereinabove to safely and automatically sever an umbilical cord positioned between blade 134 and a cutting surface 146 formed on second arm 130 when applicator 126 is moved to a closed position.

Applicator 126 also includes mounting means, for mounting a pair of umbilical cord clips 70, in the form of transversely projecting pins 148, similar to pins 114/118 noted above, which are adapted to releasably engage grooved areas 82 and 84 of clips 70. Pins 148 may be of the cylindrical or conical tapered variety as described with respect to pins 114*a*/118*a* and 114*b*/118*b* hereinabove.

Additionally, applicator 126 may include further maintenance or mounting means in the forms of proximally extending projections 150 engagable with lock catches 94 in a manner similar to projection 104 described hereinabove and projections 152 having lips 154 engagable with living hinge 80 similar to projections 120 and lips 122 described hereinabove. Projections 156 formed on first arm 128, similar to projections 124 on applicator 106, are provided to cam projections 120 and lip 122 out of engagement with living hinges 80 in a manner similar to that described hereinabove.

In using applicator 126, clips 70 are mounted on applicator 126 by means of pins 148 in grooved portions 82 and 84. An umbilical cord is positioned between arms 128 and 130 and the arms are closed to lock a clip 70 about each of the maternal and fetal sides of the umbilical cord. As clips 70 are applied to the cord, blade 134 safely and automatically moves from its recessed position to its uppermost position where it cuts through or severs the cord and abuts cutting surface 146. In this manner, applicator 126 applies a single umbilical cord clip to the maternal and fetal sides of the umbilical cord and severs the cord therebetween. In contrast to applicators 12 and 106, applicator 126 does not have integral clamping surfaces and can be removed from the cord after the clips have been applied and released. Applicator 126 remains in a closed and locked state similar to that of applicator 12 to maintain now deflected blade 134 against cutting surface 146 thereby protecting the user from blade 134 after applying clips 70 and severing the umbilical cord.

It will be understood that various modifications can be made to the embodiments of the present invention herein disclosed without departing from the spirit and scope thereof. For example, various sizes of the instrument are contemplated, as well as various types of construction materials. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A surgical instrument for clamping and severing an umbilical cord comprising:

a) a first arm having a first clamping surface;

b) a second arm movably affixed to said first arm and having a second clamping surface; and c) a severing mechanism mounted for movement with respect to said first and second arms, said severing mechanism at least partially movable relative to said first and second arms solely in response to closure of said first and second arms about an umbilical cord to sever the umbilical cord clamped therebetween.

2. The surgical instrument as recited in claim 1 further comprising a latch mechanism associated with said first and second arms for maintaining said first and second arms in a closed position about the umbilical cord.

3. A surgical instrument for clamping and severing an umbilical cord comprising:
   a) a first arm having a first clamping surface;
   b) a second arm movably affixed to said first arm and having a second clamping surface; and
   c) a severing mechanism mounted for movement with respect to said first and second arms, said severing mechanism at lest partially movable relative to said first and second arms by closure of said first and second arms about an umbilical cord to sever the umbilical cord clamped therebetween said severing mechanism including
      i) a movable knife assembly having a knife blade, said assembly operatively associated with said first arm for moving said knife blade between a first position within said first arm to a second position projecting from said first arm; and
      ii) an actuation member affixed to said second arm for actuating said knife assembly to move said knife blade between said first and second positions upon closure of said first and second arms about the umbilical cord.

4. The surgical instrument as recited in claim 3, wherein said moveable knife assembly includes:
   a) a carrier member pivotally associated with said first arm and holding said knife blade;
   b) a wedge member slidably disposed within said first arm and engagable with said carrier member to move said knife blade between said first and second positions; and
   c) a cam member pivotally affixed to said first arm, wherein said cam member is engagable with said actuation member upon closure of said first and second arms about the umbilical cord and urges said wedge member into engagement with said carrier member.

5. A surgical instrument for clamping and severing an umbilical cord and applying an umbilical cord clip about a section of the cord, the clip having a first clamping leg, a second clamping leg movably affixed to the first clamping leg and lock means for holding the first and second clamping legs about the umbilical cord, said surgical instrument comprising:
   a) a first arm having a first clamping surface;
   b) a second arm movably affixed to said first arm and having a second clamping surface;
   c) a severing mechanism mounted for movement with respect to said first and second arms, said severing mechanism at least partially movable relative to said first and second arms by closure of said first and second arms about an umbilical cord to sever the umbilical cord clamped therebetween;
   d) mounting means associated with at least one of said first and second arms and configured for engagement with corresponding mounting means on at least one of the first and second clamping legs of the clip to maintain the clip in position on the surgical instrument; and
   e) means for ejecting the clip from said first and second arms including a rigid post formed on said second arm and a flexible post formed on said first arm and configured to abut the clip, wherein closure of said first and second arms causes said rigid post to engage and deflect said flexible post to force the abutting clip away from said first and second arms.

6. The surgical instrument as recited in claim 5, wherein said mounting means of the surgical instrument includes an elongated tab member projecting transversely from at least one of said first and second arms, said tab member configured to be releasably engagable with the mounting means on at least one of the first and second clamping legs.

7. The surgical instrument as recited in claim 5, wherein said mounting means of the surgical instrument includes a pair of longitudinally spaced pins, said pins projecting transversely from at least one of said arms and configured for engagement with the corresponding mounting means on at least one of the first and second clamping legs.

8. The surgical instrument as recited in claim 5, wherein said mounting means of the surgical instrument includes a proximally extending projection formed at a distal end of at least one of said first and second arms and configured for engagement with at least a portion of the lock means on the clip to maintain the clip in position on said surgical instrument.

9. The surgical instrument as recited in claim 8, wherein said proximally extending projection is configured to engage a first portion of the lock means, said projection being cammed out of engagement with the first portion by a second portion of the lock means upon closure of the clip about the umbilical cord to release the clip from the surgical instrument.

10. The surgical instrument as recited in claim 5, wherein said mounting means of the surgical instrument includes a transversely extending projection formed on a proximal end of one of said first and second arms, said projection configured for engagement with the umbilical cord clip to maintain the clip in position on the surgical instrument during closure of the clip about the umbilical cord.

11. The surgical instrument as recited in claim 10, further comprising a projection formed on the other of said first and second arms and engagable with said transversely extending projection upon closure of said first and second arms to cam said transversely extending projection out of engagement with said clip.

12. The surgical instrument as recited in claim 5, wherein said severing mechanism includes:
   a) a deflectable knife member movably mounted with respect to said first arm; and
   b) a projection mounted on said second arm and extending towards said first arm, wherein closure of said first and second arms about the umbilical cord causes said projection to deflect said knife member away from said first arm and towards said second arm to sever the umbilical cord captured between said first and second arms.

13. An applicator and umbilical cord clip for clamping an umbilical cord, applying an umbilical cord clip to the umbilical cord and severing the cord intermediate the clamped and clipped sides of the umbilical cord, comprising:
   a) an applicator having;
      i) a first arm having a first clamping surface;
      ii) a second arm movably affixed to said first arm and having a second clamping surface;
      iii) means positioned on at least one of said first and second arms for mounting at least one umbilical cord clip thereon;
      iv) a recessed severing mechanism operatively associated with and mounted for movement with respect to said first and second arms and disposed intermediate said first and second clamping surfaces and said mounting means, said severing mechanism at least partially movable relative to said first and second arms solely in response to closure of said first and second arms about an umbilical cord to sever the cord between said first and second clamping surfaces and said clip;

b) said umbilical cord clip having;
  i) a first leg having a first clamping surface;
  ii) a second leg having a second clamping surface, said second leg movably affixed to said first leg;
  iii) lock means associated with said first and second legs for maintaining said first and second legs in a closed position about an umbilical cord; and
  iv) attachment means positioned on at least one of said first and second legs, said attachment means releasably engagable with said mounting means to hold said umbilical cord clip on said applicator.

14. An applicator and umbilical core clip for clamping an umbilical cord, applying an umbilical cord clip to the umbilical cord and severing the cord intermediate the clamped and clipped sides of the umbilical cord, comprising:

a) an applicator having;
  i) a first arm having a first clamping surface;
  ii) a second arm movably affixed to said first arm and having a second clamping surface;
  iii) means positioned on at least one of said first and second arms for mounting at least one umbilical cord clip thereon;
  iv) a recessed severing mechanism mounted for movement with respect to said first and second arms and disposed intermediate said first and second clamping surfaces and said mounting means, said severing mechanism at least partially movable relative to said first and second arms by closure of said first and second arms about an umbilical cord to sever the cord between said first and second clamping surfaces and said clip, b) said umbilical cord clip having;
  i) a first leg having a first clamping surface;
  ii) a second leg having a second clamping surface, said second leg movably affixed to said first leg:
  iii) lock means associated with said first and second legs for maintaining said first and second legs in a closed position about an umbilical cord; and
  iv) attachment means associated with at least one of said first and second legs, said attachment means releasably engagable with said mounting means to hold said umbilical cord clip on said applicator; said severing mechanism including
    A) a deflectable knife member movably mounted with respect to said first arm; and
    B) a projection mounted on said second arm and extending towards said first arm, wherein closure of said first and second arms about the umbilical cord causes said projection to deflect said knife member away from said first arm and towards said second arm to sever the umbilical cord captured between said first and second arms and said clip.

15. The applicator and umbilical cord clip as recited in claim 14, wherein said first and second legs are connected by a living hinge portion, said living hinge portion biasing said first and second legs apart in an unclamped position.

16. The applicator and umbilical cord clip as recited in claim 14, wherein said first and second clamping surfaces of said first and second legs are ridged to enhance grasping the umbilical cord.

17. The applicator and umbilical cord clip as recited in claim 14, wherein at least one of said first and second legs are hollowed beneath said clamping surfaces to provide a degree of flexibility to said clamping surfaces to prevent crushing of the umbilical cord upon clamping.

18. The applicator and umbilical cord clip as recited in claim 14, wherein said lock means includes;
  a) a lock tab projecting from a distal end of said second leg, said lock tab having a relatively straight portion extending downward toward said first leg and a hook portion formed on an end of said straight portion, said hook portion extending proximally substantially perpendicular to said straight portion, said hook portion terminating in a lip portion extending upwardly towards said second leg substantially parallel to said straight portion;
  b) a lock catch projecting distally from a distal end of said first leg and defining a recess for acceptance of said hook portion in said closed position, said lock catch having a pair of transversely spaced distally facing projections defining a channel therebetween to guide said hook portion into engagement with said recess of said lock catch.

19. An applicator for applying a first umbilical cord clip to a maternal side of the cord, applying a second umbilical cord clip to the fetal side of the cord and severing the cord intermediate the clipped maternal and fetal sides of the cord, said applicator comprising:

a) a first arm;
b) a second arm flexibly affixed to said first arm;
c) first means positioned on at least one of said first and second arms for mounting a first umbilical cord clip thereon;
d) second means positioned on at least one of said first and second arms for mounting a second umbilical cord clip thereon; and
e) a severing mechanism operatively associated with said first and second arms and disposed intermediate said first and second mounting means, said severing mechanism at least partially moveable relative to said first and second arms and actuable solely in response to closure of said first and second arms about an umbilical cord to sever the cord between the first and second umbilical cord clips.

20. The applicator as recited in claim 19, wherein said severing mechanism includes:
  a) a deflectable knife member movably mounted with respect to said first arm; and
  b) a projection mounted on said second arm and extending towards said first arm, wherein closure of said first and second arms about the umbilical cord causes said projection to deflect said knife member away from said first arm and towards said second arm to sever the umbilical cord captured between said first and second clips.

21. The applicator as recited in claim 19, wherein at least one of said first and second mounting means includes a pair of longitudinal spaced pins, said pins projecting transversely from at least one of said arms and are configured for engagement with corresponding mounting means on at least one of the first and second umbilical cord clips.

22. The applicator as recited in claim 21, wherein at least one pin of said pair of pins is cylindrical.

23. The applicator as recited in claim 21, wherein at least one pin of said pair of pins is conical.

* * * * *